United States Patent [19]

Koella

[11] 4,161,530

[45] Jul. 17, 1979

[54] PHARMACEUTICAL COMBINATION PREPARATIONS AS HYPNOTICS

[75] Inventor: Werner P. Koella, Oberwill, Switzerland

[73] Assignee: Ciba-Geigy Corporation, Ardsley, N.Y.

[21] Appl. No.: 887,687

[22] Filed: Mar. 17, 1978

Related U.S. Application Data

[63] Continuation of Ser. No. 641,318, Dec. 16, 1975, abandoned.

[30] Foreign Application Priority Data

Jan. 6, 1975 [CH] Switzerland .............................. 72/75

[51] Int. Cl.$^2$ .................. A61K 31/40; A61K 31/135; A61K 31/165; A61K 31/335

[52] U.S. Cl. .................................. 424/274; 424/279; 424/324; 424/325; 424/330

[58] Field of Search ............... 424/324, 325, 274, 330, 424/279

[56] References Cited

U.S. PATENT DOCUMENTS

| | | | |
|---|---|---|---|
| 3,857,873 | 12/1974 | Schwender et al. ............. | 260/471 R |
| 3,872,147 | 3/1975 | Köppe et al. .................... | 260/465 E |
| 3,935,267 | 1/1976 | Hauck et al. ..................... | 260/570.7 |
| 3,937,838 | 2/1976 | Wetterlin ............................ | 424/311 |

*Primary Examiner*—Allen J. Robinson
*Attorney, Agent, or Firm*—John J. Maitner

[57] ABSTRACT

Pharmaceutical Combination Preparations useful as hypnotics which contain as pharmacological active compounds a beta-receptor-blocking compound and L-tryptophane or a non-toxic salt thereof.

15 Claims, No Drawings

PHARMACEUTICAL COMBINATION PREPARATIONS AS HYPNOTICS

This is a continuation of application Ser. No. 641,318, filed on Dec. 16, 1975, now abandoned.

The present invention relates to new pharmaceutical preparations which contain, as pharmacological active compounds, a beta-receptor-blocking compound and L-tryptophane or a non-toxic salt thereof which can be used pharmaceutically.

The new pharmaceutical preparations are suitable, above all, as hypnotics for inducing and prolonging sleep and for relieving sleep disorders.

It is known that serotonin (5-hydroxy-tryptamine) plays an important part in the central nervous system as a neurohumoral information transmission agent in connection with sleep-regulating functions. Thus, for example, a lowering in the serotonin concentration in the brain, for example due to inhibition of tryptophanehydroxylase by means of α-(4-chlorophenyl)-alanine in cats (Koella et al, Electroenceph. Clin. Neurophysiol., Volume 25, page 481-490 (1968)), leads to a pronounced reduction in sleep, whilst an increase in the serotonin content, for example by intravenous or intracarotidal administration of serotonin to cats (Koella et al., Amer. J. Physiol., Volume 211, pages 926-934 (1966)), after an initial rapidly induced sleep with a short latent period and a subsequent brief phase of wakefulness, produces longer lasting periods of slow sleep (NREM sleep=Non-Rapid-Eye-Movement sleep or SWS=Slow-Wave-Sleep or slow, inactive, orthodox sleep) with marked suppression of paradoxical sleep (REM sleep=Rapid-Eye-Movement sleep or rapid, active paradoxical sleep). It has also been found that the content of serotonin in the brain varies parallel to the phases of wakefulness or sleep; see Quay, Life Sci. Volume 4, page 379 (1965) and Schering et al., Am. J. Physiol., Volume 214, page 166 (1968).

Jouvet et al., C.R. Acad. Sci. Paris, Volume 264, page 360-362 (1967), used, in place of serotonin, the biological precursor thereof, that is L-5-hydroxy-tryptophane, in order thus to achieve enrichment of serotonin; they were able to observe, for example, prolongation of slow sleep and suppression of paradoxical sleep in cats. L-Tryptophane, the biological precursor of 5-hydroxytryptophane, has also been used; thus, Williams, J. Psychiat. Res., Volume 8, pages 445-4,781 (1971), was able to achieve a considerable prolongation of slow sleep by the oral administration of high doses, for example of 7.5 g of L-tryptophane, to healthy humans.

It has now been found, surprisingly, that when a beta-receptor-blocking compound and L-tryptophane, or a non-toxic salt thereof which can be used pharmaceutically, are administered simultaneously it is possible considerably to reduce the high dose of the latter, that is to say from oral doses of about 5 to about 10 g to doses of about 0.2 g to about 2 g, and, at the same time to bring about considerable prolongation of slow sleep.

In a test with cats it can be shown that when a beta-receptor-blocking active compound and L-tryptophane, or a non-toxic salt thereof which can be used pharmaceutically, are administered simultaneously and intraperitoneally in doses in which the individual components are without any significant action, for example in doses of about 0.0003 g/kg, of L-1-(2-allyloxyphenyloxy)-3-isopropylamino-2-propanol or of a non-toxic salt thereof which can be used pharmaceutically, and of about 0.02 g/kg. of L-tryptophane or a non-toxic salt thereof which can be used pharmaceutically, it is possible to achieve distinct prolongation of sleep without a substantial change in the relative proportion of REM sleep.

Thus, a preparation for pharmaceutical purposes which is outstandingly suitable for the treatment of sleep disorders is provided by the combination of a beta-receptor-blocking active compound and L-tryptophane, or a non-toxic salt thereof which can be used pharmaceutically, and this preparation contains, for the first time, a compound which has a direct relationship with the physiology of sleep, namely L-tryptophane, in doses which can reasonably be used therapeutically.

Compounds with beta-receptor-blocking properties are, in particular, those of the formula

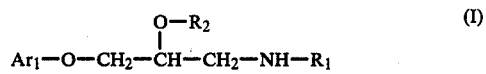

$$Ar_1-O-CH_2-\underset{\underset{O-R_2}{|}}{CH}-CH_2-NH-R_1 \qquad (I)$$

wherein $Ar_1$ represents a monocyclic or polycyclic, carbocyclic or heterocyclic radical which contains at least one ring of aromatic character and which is bonded to the oxygen atom via a ring carbon atom, preferably of the ring of aromatic character, $R_1$ denotes an optionally substituted aliphatic, cycloaliphatic or araliphatic hydrocarbon radical and $R_2$ represents hydrogen or the acyl radical of an organic carboxylic acid, as well as non-toxic salts thereof which can be used pharmaceutically, above all corresponding acid addition salts thereof.

Carbocyclic radicals $Ar_1$ of aromatic character are, above all, phenyl, as well as optionally partially saturated bicyclic aromatic hydrocarbon radicals, such as naphthyl, for example 1- or 2-naphthyl, 1,2,3,4-tetrahydro-benz-naphthyl, for example, 1,2,3,4-tetrahydro-5-naphthyl, benz-indenyl, for example 4- or 5-indenyl, or benz-indanyl, for example 4- or 5-indanyl, and also optionally partially saturated polycyclic aromatic hydrocarbon radicals, such as benz-fluorenyl, for example 4-fluorenyl, or 9,10-ethano-9,10-dihydro-benz-anthryl, for example 9,10-ethano-9,10-dihydro-1-anthryl, partially saturated radicals of the above type being bonded to the oxygen atom via a ring carbon atom of the aromatic part.

Heterocyclic radicals $Ar_1$ contain, as ring heteroatoms, above all one or more ring nitrogen atoms as well as, preferably in addition to a ring nitrogen atom, also a ring oxygen atom or ring sulphur atom. Such radicals are, in particular, monocyclic, five-membered or six-membered, mono-, di- or tri-azacyclic radicals, above all monocyclic, monoazacyclic, six-membered radicals of aromatic character, such as pyridyl, for example 2-, 3- or 4-pyridyl, monocyclic, diazacyclic, six-membered radicals of aromatic character, such as pyridazinyl, for example 3-pyridazinyl, pyrimidinyl, for example 2- or 4-pyrimidinyl, or pyrazinyl, for example 2-pyrazinyl, monocyclic, thiadiazacyclic, five-membered radicals of aromatic character, such as thiadiazolyl, for example 1,2,5-thiadiazol-3-yl, optionally partially saturated bicyclic, monoazacyclic radicals of aromatic character with a five-membered or six-membered heterocyclic ring, such as indolyl, for example 4-indolyl, or optionally partially saturated quinolinyl, for example 1,2,3,4-tetrahydro-5-quinolinyl, or bicyclic monothiacyclic radicals of partially aromatic character, such as 2H-thiochromenyl, for example 2H-8-thiochromenyl.

The above radicals $Ar_1$ can be unsubstituted or substituted and $Ar_1$ contains above all one, or also several, in particular two, substituents. The latter are, above all, optionally substituted aliphatic or cycloaliphatic hydrocarbon radicals, optionally etherified or esterified hydroxyl or mercapto groups, acyl radicals, optionally functionally modified carboxyl groups, nitro or optionally substituted amino groups. Saturated parts of the group $Ar_1$ can also contain, in addition to the above-mentioned substituents, substituents which have two bonds, above all oxo.

As substituents of the radical $Ar_1$, aliphatic hydrocarbon radicals are, in particular, lower alkyl or lower alkenyl, as well as lower alkinyl. Substituents of such radicals, especially of lower alkyl, as well as lower alkenyl, are optionally etherified or esterified hydroxyl, for example lower alkoxy, lower alkylthio or halogen, optionally functionally modified carboxyl, especially optionally N-substituted carbamoyl, such as N-lower alkylated carbamoyl, or optionally substituted amino, especially acylamino, wherein acyl represents the radical of an organic carboxylic acid or of a carbonic acid half-derivative, as well as of an organic sulphonic acid, such as lower alkanoylamino, lower alkoxycarbonylamino or optionally N-substituted ureido, such as N'-lower alkylated ureido, for example ureido, N'-lower alkyl-ureido or N',N'-di-lower alkyl-ureido, and also lower alkylsulphonylamino. Substituted lower alkyl radicals are, above all, hydroxy-lower alkyl, lower alkoxy-lower alkyl, lower alkylthio-lower alkyl, halogeno-lower alkyl, optionally N-lower alkylated carbamoyl-lower alkyl, lower alkanoylamino-lower alkyl or lower alkoxycarbonylamino-lower alkyl, and also lower alkanoylamino-lower alkenyl or lower alkoxycarbonylamino-lower alkenyl.

Cycloaliphatic hydrocarbon radicals are represented, in particular, by monocyclic and polycyclic cycloalkyl.

As substituents of a radical $Ar_1$, etherified hydroxyl or mercapto groups are, above all, hydroxyl or mercapto which are etherified by optionally substituted aliphatic hydrocarbon radicals, such as lower alkoxy lower alkenyloxy or lower alkinyloxy, and also lower alkylthio or lower alkenylthio. Substituents of such etherifying aliphatic hydrocarbon radicals, especially of etherifying lower alkyl, are, above all, optionally etherified or esterified hydroxyl or mercapto, such as lower alkoxy, lower alkylthio or halogen, or optionally substituted amino, such as acylamino, for example lower alkanoylamino or lower alkoxycarbonylamino. Hydroxyl or mercapto etherified by correspondingly substituted aliphatic hydrocarbon radicals is, in particular, lower alkoxy-lower alkoxy, lower alkylthio-lower alkoxy or lower alkoxy-lower alkylthio and also lower alkanoylamino-lower alkoxy or lower alkoxycarbonylamino-lower alkoxy.

As substituents of groups $Ar_1$, esterified hydroxyl or mercapto groups are, above all, halogen as well as lower alkanoyloxy.

As substituents of the radical $Ar_1$, acyl groups represent, above all, lower alkanoyl.

As substituents of $Ar_1$, optionally functionally modified carboxyl groups are, in particular, esterified or amidated carboxyl and also cyano. Esterified carboxyl is, above all, lower alkoxycarbonyl, whilst amidated carboxyl represents optionally substituted carbamoyl, such as carbamoyl, N-lower alkyl-carbamoyl or N,N-di-lower alkyl-carbamoyl.

As substituents of groups $Ar_1$, optionally substituted amino groups are, in particular, acylamino, wherein acyl above all represents the corresponding radical of an organic carboxylic acid or of a half-derivative of carbonic acid, and also of an organic sulphonic acid, such as lower alkanoylamino, lower alkoxycarbonylamino or optionally N'-lower alkylated ureido, for example ureido, N'-lower alkyl-ureido or N',N'-di-lower alkyl-ureido, and also lower alkylsulphonylamino as well as N-lower alkylated amino, such as N-lower alkylamino or N,N-di-lower alkylamino, and optionally unsaturated N,N-lower alkyleneamino, N,N-aza-lower alkyleneamino, N,N-oxa-lower alkyleneamino or N,N-thia-lower alkyleneamino.

Aliphatic hydrocarbon radicals $R_1$ are, above all, lower alkyl, especially lower alkyl branched at the linking carbon, and also lower alkenyl or lower alkinyl, whilst cycloaliphatic hydrocarbon radicals represent, in particular, cycloalkyl, including polycyclic cycloalkyl, and araliphatic hydrocarbon radicals represent, above all, phenyl-lower alkyl. Substituents of such hydrocarbon radicals are, for example for lower alkyl, etherified hydroxyl, especially phenoxy or pyridyloxy which are optionally substituted, for example by functionally modified carboxyl, such as optionally N-lower alkylated carbamoyl, for example carbamoyl, N-lower alkyl-carbamoyl, or N,N-di-lower alkyl-carbamoyl, or optionally functionally modified carboxyl, such as carboxyl and esterified carboxyl, for example lower alkoxycarbonyl, amidated carboxyl, such as optionally N-lower alkylated carbamoyl, for example carbamoyl, N-lower alkyl-carbamoyl or N,N-di-lower alkyl-carbamoyl, or cyano, and, for example for the aromatic part of phenyl-lower alkyl, optionally functionally modified carboxyl, above all amidated carboxyl, such as optionally N-lower alkylated carbamoyl or N,N-di-lower alkylated carbamoyl. Lower alkyl radicals substituted in this way are phenoxy-lower alkyl or preferably optionally N-alkylated carbamoylphenoxy-lower alkyl, and also pyridyloxy-lower alkyl or preferably optionally N-lower alkylated carbamoylpyridyloxy-lower alkyl and also lower alkoxycarbonyl-lower alkyl, optionally N-lower alkylated carbamoyl-lower alkyl or cyano-lower alkyl.

An acyl radical $R_2$ is, above all, the corresponding radical of an organic carboxylic acid, especially lower alkanoyl or benzoyl.

Unless specific data are given, the radicals and compounds designated "lower" in the preceding and following text preferably contain up to 7 carbon atoms, monovalent radicals contain above all up to 5 carbon atoms and divalent radicals contain 3 to 6, above all 4 or 5, carbon atoms.

Unless specific data are given, the general concepts used in the preceding and the following text preferably have the following meanings:

Lower alkyl is, for example, methyl, ethyl, n-propyl, isopropyl, n-butyl, isobutyl, sec.-butyl or tert.-butyl as well as n-pentyl, isopentyl, neopentyl, n-hexyl, isohexyl or n-heptyl. Lower alkyl branched at the linking carbon atom is, above all, isopropyl or tert.-butyl.

Lower alkenyl is above all allyl and also vinyl, 2-methyl-allyl, 2-butenyl or 3,3-dimethylallyl, whilst lower alkinyl is, for example, ethinyl or propargyl.

Lower alkoxy is, for example, methoxy, ethoxy, n-propoxy, isopropoxy, n-butoxy, isobutoxy or tert.-butoxy.

Lower alkylthio is, for example, methylthio, ethylthio, isopropylthio or n-butylthio.

Halogen is, for example, chlorine or bromine and also fluorine as well as iodine.

Optionally N-lower alkylated carbamoyl is, for example, carbamoyl and also N-lower alkyl-carbamoyl, such as N-methyl-carbamoyl or N-ethyl-carbamoyl, or N,N-di-lower alkyl-carbamoyl, such as N,N-dimethyl-carbamoyl or N,N-diethyl-carbamoyl.

Lower alkanoylamino is, for example, formylamino, acetylamino, propionylamino, butyrylamino or pivaloylamino.

Lower alkoxycarbonylamino is, for example, methoxycarbonylamino, ethoxycarbonylamino or tert.-butoxycarbonylamino, whilst N'-lower alkyl-ureido and N',N'-di-lower alkyl-ureido are, for example, N'-methylureido, N'-ethylureido, N',N'-dimethylureido or N',N'-diethylureido.

Lower alkylsulphonylamino is, for example, methylsulphonylamino or ethylsulphonylamino.

Hydroxy-lower alkyl is, for example, hydroxymethyl or 1- or 2-hydroxyethyl.

Lower alkoxy-lower alkyl is, for example, lower alkoxymethyl or, preferably, 2-(lower alkoxy)-ethyl, such as methoxymethyl, ethoxymethyl, 2-methoxyethyl, 2-ethoxy-ethyl or 2-isopropoxy-ethyl.

Lower alkylthio-lower alkyl is, for example, lower alkylthio-methyl or, in particular, 2-(lower alkylthio)-ethyl, for example methylthiomethyl, ethylthiomethyl, 2-methylthioethyl or 2-ethylthioethyl.

Halogeno-lower alkyl is, in particular, trifluoromethyl.

Optionally N-lower alkylated carbamoyl-lower alkyl is, for example, carbamoylmethyl or 1- or 2-carbamoylethyl and also N-lower alkyl-carbamoyl-lower alkyl, such as N-methylcarbamoylmethyl or 1- or 2-N-methylcarbamoyl-ethyl, or N,N-di-lower alkyl-carbamoyl-lower alkyl, such as N,N-dimethylcarbamoylmethyl or 1- or 2-N,N-dimethylcarbamoyl-ethyl.

Lower alkanoylamino-lower alkyl is, for example, lower alkanoylaminomethyl or, preferably, 2-lower alkanoylaminoethyl, such as acetylaminomethyl, propionylaminomethyl, 2-acetylaminoethyl, 2-propionylaminoethyl or 2-pivaloylaminoethyl, whilst lower alkoxycarbonylamino-lower alkyl represents, for example, lower alkoxycarbonylamino-methyl or, preferably, 2-lower alkoxycarbonylamino-ethyl, such as methoxycarbonylaminomethyl, ethoxycarbonylaminomethyl, 2-methoxycarbonylaminoethyl, 2-ethoxycarbonylaminoethyl or 2-tert.-butoxycarbonylaminoethyl.

Lower alkanoylamino-lower alkenyl is, in particular, 2-lower alkanoylamino-vinyl, for example 2-acetylamino-vinyl, 2-propionylamino-vinyl or 2-pivaloylamino-vinyl, whilst lower alkoxycarbonylamino-lower alkenyl preferably represents 2-lower alkoxycarbonylamino-vinyl, such as 2-methoxycarbonylamino-vinyl, 2-ethoxycarbonylamino-vinyl or 2-tert.-butoxycarbonylamino-vinyl.

Cycloalkyl, including polycyclic cycloalkyl, preferably contains 3–10 ring carbon atoms and denotes cyclopropyl or, in particular, cyclopentyl or cyclohexyl, as well as adamantyl, such as 1-adamantyl.

Lower alkenyloxy is, in particular, allyloxy as well as 2-methylallyloxy, and also vinyloxy, 2-butenyloxy or 3,3-dimethylallyloxy, whilst lower alkinyloxy represents, for example, propargyloxy.

Lower alkenylthio is, for example, allylthio and also 2-methyl-allylthio or 2-butenylthio.

In a lower alkoxy-lower alkoxy radical the two oxygen atoms are preferably separated by at least 2, for example by 2–3, carbon atoms; such radicals are thus, for example, methoxymethoxy or ethoxymethoxy but above all 2-(lower alkoxy)-ethoxy, for example 2-methoxyethoxy or 2-ethoxyethoxy, as well as 3-(lower alkoxy)-propoxy, for example 3-methoxy-propoxy or 3-ethoxy-propoxy.

In a lower alkylthio-lower alkoxy radical the sulphur atom and the oxygen atom are preferably separated from one another by at least 2, for example by 2–3, carbon atoms; such radicals are thus, above all, 2-(lower alkylthio)-ethoxy, for example 2-methylthio-ethoxy or 2-ethylthio-ethoxy.

In a lower alkoxy-lower alkylthio radical the oxygen atom and the sulphur atom are likewise preferably separated from one another by at least 2, for example by 2–3, carbon atoms; such radicals are, above all, 2-(lower alkoxy)-ethylthio, for example 2-methoxy-ethylthio or 2-ethoxy-ethylthio.

In lower alkanoylamino-lower alkoxy radicals and lower alkoxycarbonylamino-lower alkoxy radicals the nitrogen atom and the linking oxygen atom are preferably separated from one another by at least 2, for example 2–3, carbon atoms; these radicals are, above all, 2-lower alkanoylamino-ethoxy, for example 2-acetylamino-ethoxy, 2-propionylamino-ethoxy or 2-pivaloylamino-ethoxy, or 2-lower alkoxycarbonylamino-ethoxy, for example 2-methoxycarbonylamino-ethoxy or 2-ethoxycarbonylamino-ethoxy.

Lower alkanoyloxy is, for example, acetyloxy, propionyloxy or pivaloyloxy.

Lower alkanoyl is, in particular, acetyl, propionyl or pivaloyl.

Lower alkoxycarbonyl is, for example, methoxycarbonyl, ethoxycarbonyl or tert.-butoxycarbonyl.

N-Lower alkylamino and N,N-di-lower alkylamino are, for example, methylamino, ethylamino, dimethylamino or diethylamino.

Optionally unsaturated N,N-lower alkyleneamino preferably contains 5–7 ring members and is, in particular, pyrrolidino or piperidino, and also 1-pyrryl, whilst N,N-aza-lower alkyleneamino, N,N-oxa-lower alkyleneamino and N,N-thia-lower alkyleneamino preferably contain 6 ring members, the second ring heteroatom being separated from the linking nitrogen atom by 2 carbon atoms and, in the N,N-aza-lower alkyleneamino radical, being optionally substituted, for example by lower alkyl; such radicals are, for example, 4-methyl-1-piperazino, 4-morpholino or 4-thiomorpholino.

Phenyl-lower alkyl is, for example, benzyl or 1- or 2-phenylethyl.

Pyridyloxy is, for example, 2-pyridyloxy, 3-pyridyloxy or 4-pyridyloxy.

In a phenoxy-lower alkyl radical and pyridyloxy-lower alkyl radical $R_1$, which preferably contain optionally N-lower alkylated carbamoyl as substituents, the oxygen atom and the linking carbon atom bonded to the nitrogen atom are preferably separated from one another by at least 2, for example by 2–3, carbon atoms. Such substituents are, in particular, 2-(optionally N-lower alkylated carbamoyl-phenoxy)-lower alkyl, for example 2-(2-carbamoylphenoxy)-ethyl, 2-(4-carbamoylphenoxy)-ethyl, 2-(2-N-methylcarbamoylphenoxy)-ethyl or 2-(4-N,N-dimethylcarbamoylphenoxy)-ethyl, and also 2-(optionally N-lower alkylated carbamoyl-pyridyloxy)-lower alkyl, for example 2-(4-carbamoyl-2-pyridyloxy)-ethyl, 2-(2-carbamoyl-4-pyridyloxy)-ethyl or 2-(3-carbamoyl-2-pyridyloxy)-ethyl.

Lower alkoxycarbonyl-lower alkyl is, for example, lower alkoxycarbonylmethyl or 1-lower alkoxycarbonyl-2-propyl, for example methoxycarbonylmethyl, ethoxycarbonylmethyl, 1-methoxycarbonyl-2-propyl or 1-ethoxycarbonyl-2-propyl.

Optionally N-lower alkylated carbamoyl-lower alkyl is, above all, carbamoylmethyl and also N-lower alkyl-carbamoylmethyl or N,N-di-lower alkylcarbamoylmethyl, for example N-methylcarbamoylmethyl, N-ethylcarbamoylmethyl, N,N-dimethylcarbamoylmethyl or N,N-diethylcarbamoylmethyl, as well as 1-carbamoyl-2-propyl and also 1-N-lower alkyl-carbamoyl-2-propyl or 1-N,N-di-lower alkyl-carbamoyl-2-propyl, for example 1-N-methylcarbamoyl-2-propyl, 1-N-ethylcarbamoyl-2-propyl, 1-N,N-dimethylcarbamoyl-2-propyl or 1-N,N-diethylcarbamoyl-2-propyl.

Cyano-lower alkyl is, for example, cyanomethyl or 1-cyano-2-propyl.

In the compounds of the formula I, the group $Ar_1$ preferably denotes naphthyl, for example 1-naphthyl, fluorenyl, for example 4-fluorenyl, 9,10-ethano-9,10-dihydro-anthryl, for example 9,10-ethano-9,10-dihydro-1-anthryl, indolyl, for example 4-indolyl, 2H-thiochromenyl, for example 2H-8-thiochromenyl, lower alkyl-phenyl, such as methyl-phenyl, for example 2- or 3-methyl-phenyl, halogeno-lower alkyl-phenyl, such as chloromethyl-phenyl, for example 2-chloro-5-methyl-phenyl, lower alkenyl-phenyl, such as allylphenyl, for example 2-allylphenyl, lower alkinyl-phenyl, such as ethinyl-phenyl, for example 2-ethinyl-phenyl, cycloalkyl-phenyl, for example 2-cyclopropyl-phenyl or 2-cyclopentyl-phenyl, hydroxy-lower alkyl-phenyl, for example 2-hydroxymethyl-phenyl, lower alkoxy-lower alkyl-phenyl, such as lower alkoxymethyl-phenyl or (2-lower alkoxy-ethyl)-phenyl, for example 2-methoxymethylphenyl or 4-(2-methoxyethyl)-phenyl, carbamoyl-lower alkylphenyl, for example carbamoylmethylphenyl, lower alkoxycarbonylamino-lower alkyl-phenyl, such as (2-lower alkoxycarbonylamino-ethyl)-phenyl, for example 4-(2-methoxycarbonylamino-ethyl)-phenyl, halogeno-lower alkoxycarbonylamino-lower alkyl-pyridyl, for example 3-chloro-4-(2-methoxycarbonylaminoethyl)-2-pyridyl, lower alkoxycarbonylamino-lower alkenylphenyl, especially (2-lower alkoxycarbonylamino-vinyl)-phenyl, for example 4-(2-methoxycarbonylamino-vinyl)-phenyl, lower alkoxyphenyl, such as methoxyphenyl, for example 2-methoxyphenyl, lower alkenyloxy-phenyl, such as allyloxyphenyl, for example 2-allyloxy-phenyl, or methallyloxyphenyl, for example 2-(2-methylallyloxy)-phenyl, lower alkinyloxy-phenyl, such as propargyloxy-phenyl, for example 2-propargyloxy-phenyl, lower alkylthio-lower alkoxy-phenyl wherein the sulphur atom is separated from the oxygen atom by 2–3 carbon atoms, such as (2-lower alkylthio-ethoxy)-phenyl, for example 4-(2-methylthio-ethoxy)-phenyl, lower alkylthio-phenyl, such as methylthio-phenyl, for example 2-methylthiophenyl, halogeno-phenyl, such as chlorophenyl, for example 2-chlorophenyl, lower alkanoyl-lower alkanoylamino-phenyl, for example 2-acetyl-4-n-butyrylamino-phenyl, cyano-phenyl, for example 2-cyanophenyl, lower alkanoylamino-phenyl, such as acetylaminophenyl, for example 4-acetylamino-phenyl, lower alkylsulphonylamino-phenyl, for example 4-methylsulphonylamino-phenyl, (1-pyrryl)-phenyl, for example 2-(1-pyrryl)-phenyl, morpholinothiadiazolyl, for example 4-morpholino-1,2,5-thiadiazol-3-yl, oxo-5,6,7,8-tetrahydro-benz-naphthyl, for example 5-oxo-5,6,7,8-tetrahydro-1-naphthyl, or oxo-1,2,3,4-tetrahydro-benz-quinolinyl, for example 2-oxo-1,2,3,4-tetrahydro-5-quinolinyl, $R_2$ represents, in particular, hydrogen or lower alkanoyl, for example acetyl or pivaloyl, and $R_1$ is, above all, lower alkyl, especially lower alkyl branched at the linking carbon, for example isopropyl or tert.-butyl, and also carbamoylphenoxy-lower alkyl, such as 2-carbamoylphenoxy-lower alkyl, for example 2-(4-carbamoylphenoxy)-ethyl.

Compounds with beta-receptor-blocking properties, of the above formula I, are, above all, the following compounds in which lower alkyl $R_1$ is branched at the linking carbon atom: 1-(naphthyloxy)-3-lower alkylamino-2-propanol, for example 3-isopropylamino-1-(1-naphthyloxy)-2-propanol, 1-(benz-fluorenyloxy)-3-lower alkylamino-2-propanol and the corresponding O-esters thereof with lower alkanecarboxylic acids, for example 1-(4-fluorenyloxy)-3-isopropylamino-2-propanol or 3-tert.-butylamino-1-(4-fluorenyloxy)-2-pivaloyloxy-propane, 1-(9,10-ethano-9,10-dihydro-benz-anthryloxy)-3-lower alkylamino-2-propanols, for example 1-(9,10-ethano-9,10-dihydro-1-anthryloxy)-3-isopropylamino-2-propanol, 1-(benz-indolyloxy)-3-lower alkylamino-2-propanols, for example 1-(4-indolyloxy)-3-isopropylamino-2-propanol, 3-lower alkylamino-1-(2H-benz-thiochromenyloxy)-2-propanols, for example 3-tert.-butylamino-1-(2H-8-thiochromenyloxy)-2-propanol, 3-lower alkylamino-1-(lower alkyl-phenoxy)-2-propanols wherein the phenyl radical can additionally be substituted by halogen, for example 3-isopropylamino-3-(3-methyl-phenoxy)-2-propanol, 1-(2-chloro-5-methyl)-3-isopropylamino-2-propanol or 2-tert.-butylamino-1-(2-chloro-5-methyl)-2-propanol, 3-(carbamoylphenoxy-lower alkylamino)-1-(lower alkyl-phenyl)-2-propanols, for example 3-[2-(4-carbamoylphenoxy)-ethylamino]-1-(2-methyl-phenyl)-2-propanol, 1-(lower alkenyl-phenoxy)-3-lower alkylamino-2-propanols, for example 1-(2-allyl-phenoxy)-3-isopropylamino-2-propanol, 1-(lower alkinyl-phenoxy)-3-lower alkylamino-2-propanols, for example 1-(2-ethinyl-phenoxy)-3-isopropylamino-2-propanol, 1-(cycloalkyl-phenoxy)-3-lower alkylamino-2-propanols, for example 1-(2-cyclopropyl-phenoxy)-3-isopropylamino-2-propanol or 3-tert.-butylamino-1-(2-cyclopentyl-phenoxy)-2-propanol, 1-(hydroxy-lower alkyl-phenoxy)-3-lower alkylamino-2-propanols, for example 1-(2-hydroxymethyl-phenoxy)-3-isopropylamino-2-propanol, 1-(lower alkoxy-lower alkylphenoxy)-3-lower alkylamino-2-propanols, for example 3-isopropylamino-1-(2-methoxymethyl-phenoxy)-2-propanol, 3-tert.-butylamino-1-(2-methoxymethyl-phenoxy)-2-propanol or 3-isopropylamino-1-[4-(2-methoxyethyl)-phenoxy]-2-propanol, 1-(carbamoyl-lower alkyl-phenoxy)-3-lower alkylamino-2-propanols, for example 1-(4-carbamoylmethyl-phenoxy)-3-isopropylamino-2-propanol, 1-(lower alkoxycarbonylamino-lower alkyl-phenoxy)-3-lower alkylamino-2-propanols, for example 3-isopropylamino-1-[4-(2-methoxycarbonylamino-ethyl)-phenoxy]-2-propanol, 1-(halogeno-lower alkoxycarbonylamino-lower alkyl-pyridyloxy)-3-lower alkylamino-2-propanols for example 3-[3-chloro-4-(2-methoxycabonylamino-ethyl)-2-pyridyloxy]-3-isopropylamino-2-propanol, 1-(lower alkoxycarbonylamino-vinyl-phenoxy)-3-lower alkylamino-2-propanols, for example 3-isopropylamino-1-[4-(2-methoxycarbonylamino-vinyl)-phenoxy]-2-propanol, 1-(lower alkoxy-phenoxy)-3-lower alkylamino-2-propanols, for example 3-isopropylamino-1-(2-methoxy-phenoxy)-2-propanol, 1-(lower alkenyloxyphenoxy)-3-lower alkylamino-2-propanols, for example 1-(2-allyloxy-phenoxy)-3-isopropylamino-2-propanol, 1-(2-allyloxy-phenoxy)-3-tert.-butylamino-2-propanol or 3-isopropylamino-1-(2-methylallyloxy-phenoxy)-2-propanol, 1-(lower alkinyloxy-phenoxy)-3-lower alkylamino-2-propanols, for example 3-isopropylamino-1-(2-propargyloxy-phenoxy)-2-propanol, 3-lower alkylamino-1-(lower alkylthio-lower alkoxyphenoxy)-2-propanols, wherein the sulphur atom is separated from the oxygen atom by 2–3 carbon atoms, for example 3-isopropylamino-1-[4-(2-methylthioethoxy)-phenoxy]-2-propanol, 1-(halogeno-phenoxy)-3-lower alkylamino-2-propanols, for example 3-tert.-butylamino-1-(2-chloro-phenoxy)-2-propanol, 1-(lower alkylthiophenoxy)-3-lower alkylamino-2-propanols, for example 3-isopropylamino-1-(2-methylthio-phenoxy)-2-propanol, 1-(lower alkanoyl-lower alkanoylaminophenoxy)-3-lower alkylamino-2-propanol, for example 1-(2-acetyl-4-n-butyrylaminophenoxy)-3-isopropylamino-2-propanol, 1-(cyano-phenoxy)-3-lower alkylamino-2-propanols, for example 3-tert.-butylamino-1-(2-cyano-phenoxy)-2-propanol or 1-(2-cyano-phenoxy)-3-isopropylamino-2-propanol, 1-(lower alkanoylamino-phenoxy)-3-lower alkylamino-2-propanols, for example 1-(4-acetylaminophenoxy)-3-isopropylamino-2-propanol, 3-lower alkylamino-1-(lower alkylsulphonylamino-phenoxy)-2-propanols, for example 3-isopropylamino-1-(4-methylsulphonylaminophenoxy)-2-propanol, 3-lower alkylamino-1-(1-pyrryl)-phenoxy-2-propanols, for example 3-isopropylamino-1-[2-(1-pyrryl)-phenoxy]-2-propanol, 1-(morpholinothiadiazolyloxy)-3-lower alkylamino-2-propanol, for example 3-isopropylamino-1-(4-morpholino-1,2,5-thiadiazol-3-yloxy)-2-propanol, 3-lower alkylamino-1-(oxo-5,6,7,8-tetrahydro-benz-naphthyloxy)-2-propanols, for example 3-isopropylamino-1-(5-oxo-5,6,7,8-tetrahydro-1-naphthyloxy)-2-propanol, or 3-lower alkylamino-1-(oxo-1,2,3,4-tetrahydro-benz-quinolinyloxy)-2-propanols, for example 3-isopropylamino-1-(2-oxo-1,2,3,4-tetrahydro-5-quinolinyloxy)-2-propanol or 3-tert.-butylamino-1-(2-oxo-1,2,3,4-tetrahydro-5-quinolinyloxy)-2-propanol, and non-toxic acid addition salts thereof which can be used pharmaceutically.

A further group of beta-receptor-blocking compounds can be represented by the formula

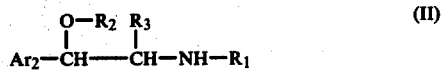

wherein $R_1$ and $R_2$ have the abovementioned meanings, $Ar_2$ represents a monocyclic or polycyclic, carbocyclic radical which contains at least one ring of aromatic character and which is bonded to the oxygen atom via a ring carbon atom, preferably of the ring of aromatic character, and $R_3$ denotes hydrogen or lower alkyl, and also comprises the salts thereof which can be used pharmaceutically, above all the corresponding acid addition salts thereof.

A carbocyclic radical $Ar_2$ of aromatic character has, for example, the meaning given above for the group $Ar_1$ and is, above all, phenyl, as well as an optionally partially saturated, bicyclic aromatic hydrocarbon radical, such as naphthyl, for example 1- or 2-naphthyl, 1,2,3,4-tetrahydro-benz-naphthyl, or benz-indanyl, for example 4- or 5-indanyl, and such radicals can be substituted, for example like the corresponding groups $Ar_1$, and contain, above all, halogen, lower alkyl, lower alkoxy, lower alkylsulphonylamino and/or nitro, for example the corresponding substituents described above.

A group $R_1$ in the above compounds of the formula II is, above all, lower alkyl, especially lower alkyl branched at the linking carbon atom, above all isopropyl or tert.-butyl.

In addition to hydrogen, $R_2$ also represents lower alkanoyl, for example acetyl or pivaloyl.

The radical $R_3$ denotes hydrogen or lower alkyl, especially methyl.

In the above compounds of the formula II, $Ar_2$ represents, for example, naphthyl, for example 1-naphthyl, lower alkoxy-phenyl, for example 2,5-dimethoxy-phenyl, halogenophenyl, for example 3,4-dichlorophenyl, nitrophenyl, for example 4-nitrophenyl, lower alkylsulphonylamino-phenyl, for example 4-methylsulphonylamino-phenyl, carbamoyl-hydroxyphenyl, for example 4-carbamoyl-3-hydroxyphenyl, or 1,2,3,4-tetrahydro-benz-naphthyl, for example 1,2,3,4-tetrahydro-5-naphthyl, $R_1$ denotes, above all, lower alkyl branched at the linking carbon atom, for example isopropyl or tert.-butyl, $R_2$ is, in particular, hydrogen and $R_3$ represents, above all, hydrogen or methyl.

Compounds of the above structural formula II which have beta-receptor-blocking properties are, above all, the following compounds in which lower alkyl $R_1$ is branched at the linking carbon atom: 1-(naphthyl)-2-lower alkylamino-ethanols, for example 2-isopropylamino-1-(1-naphthyl)-ethanol, 1-(lower alkoxyphenyl)-2-lower alkylamino-ethanols, for example 2-tert.-butylamino-1-(2,5-dimethoxy-phenyl)-ethanol, 1-(halogenophenyl)-2-lower alkylamino-ethanols, for example 1-(3,4-dichlorophenyl)-2-isopropylamineethanol, 2-lower alkylamino-1-(nitrophenyl)-2-propanols, for example 2-isopropylamino-1-(4-nitrophenyl)-propanol, 2-lower alkylamino-1-(lower alkylsulphonylamino-phenyl)-ethanols, for example 2-isopropylamino-1-(4-methylsulphonylamino-phenyl)-ethanol, 1-(carbamoylhydroxyphenyl)-2-lower alkylamino-ethanols, for example 1-(4-carbamoyl-3-hydroxyphenyl)-2-isopropylamino-ethanol or 1-(4-carbamoyl-3-hydroxyphenyl)-2-tert.-butylamino-ethanol, 2-lower alkylamino-1-(1,2,3,4-tetrahydro-benz-naphthyl)-ethanols, for example 2-tert.-butylamino-1-(1,2,3,4-tetrahydro-5-naphthyl)-ethanol, and non-toxic acid addition salts thereof which can be used pharmaceutically.

Non-toxic salts, which can be used pharmaceutically, of the abovementioned compounds with beta-receptor-blocking properties are, above all, corresponding acid addition salts with inorganic acids, for example hydrochloric, hydrobromic, nitric, sulphuric or phosphoric acids, or with organic acids, such as organic carboxylic acids, for example acetic acid, propionic acid, glycollic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-amino-salicylic acid, 2-phenoxybenzoic acid, 2-acetoxy-benzoic acid, embonic acid, nicotinic acid or isonicotinic acid, or organic sulphonic acids, for example methanesulphonic acid, ethanesulphonic acid, 2-hydroxy-ethanesulphonic acid, ethane-1,2-disulphonic acid, benzenesulphonic acid, 4-methylbenzenesulphonic acid or naphthalene-2-sulphonic acid.

The abovementioned compounds, which contain centres of asymmetry, can be used in the form of mixtures of isomers, especially of racemates, or in the form of pure isomers, especially of optically active antipodes.

Non-toxic salts, which can be used pharmaceutically, of L-tryptophane are both the corresponding acid addition salts with strong acids, especially with strong inorganic acids, for example hydrochloric, sulphuric or phosphoric acids, or with strong organic acids, especially corresponding sulphonic acids, for example methanesulphonic acid, and also salts with strong bases, especially the alkali metal salts or alkaline earth metal salts, for example sodium salts or potassium salts.

The invention relates in particular to pharmaceutical preparations which contain a beta-receptor-blocking compound, especially one of those mentioned above, together with L-tryptophane or a non-toxic salt thereof which can be used pharmaceutically, as well as to the manufacture of these preparations and also to the use of the above combination of active compounds in the form of the said preparations for the treatment of sleep disorders and for inducing and prolonging sleep.

The invention relates in particular to the new pharmaceutical preparations which contain 3-isopropylamino-1-(1-naphthyloxy)-2-propanol, 3-isopropylamine-3-(3-methylphenoxy)-2-propanol, 1-(2-allyl-phenoxy)-3-isopropylamino-2-propanol, 1-(4-acetylamino-phenoxy)-3-isopropylamino-2-propanol, 1-(4-indolyloxy)-3-isopropylamino-2-propanol, 3-isopropylamino-1-[4-(2-methoxyethyl)-phenoxy]-2-propanol, 3-isopropylamino-1-[4-(2-methylthioethoxy)-phenoxy]-2-propanol, 1-(9,10-ethane-9,10-dihydro-1-anthryloxy)-3-isopropylamino-2-propanol, 3-isopropylamino-1-[2-(1-pyrryl)-phenoxy]-2-propanol, [4-(2-methylthioethoxy)-phenoxy]-2-propanol, 1-[2-(3,4-dimethoxyphenyl)-ethylamino]-3-(3-methyl-phenoxy)-2-propanol, 1-isopropylamino-3-(1,2,3,4-tetrahydro-1,4-ethano-5-napthyloxy)-propanol, 1-tert.-butylamino-3-(1,2,3,4-tetrahydro-2,3-dihydroxy-5-napthyloxy)-2-propanol, 1-(7-indenyloxy)-3-isopropylamino-2-propanol, 1-(7-indenyloxy)-3-isopropylamino-2-propanol, 1-(5-methyl-8-cumaryloxy)-3-isopropylamino-2-propanol, 4-(3-isopropylamino-2-hydroxy-1-propyloxy)-2-methyl-indole or 2-tert.-butylamino-1-(7-ethyl-2-benzofuranyloxy)-ethanol, or above all, 1-(2-allyloxy-phenoxy)-3-isopropylamino-2-propanol or a non-toxic acid addition salt thereof, which can be used pharmaceutically, as the beta-receptor-blocking component, together with L-tryptophane or a non-toxic salt thereof which can be used pharmaceutically.

The invention relates, above all, to the new pharmaceutical preparations which contain 1-(2-allyloxy-phenoxy)-3-isopropylamino-2-propanol, 3-isopropylamino-1-(1-naphthyloxy)-2-propanol, 3-isopropylamino-1-[4-(2-methoxyethyl)-phenoxy]-2-propanol, 1-(4-acetylamino-phenoxy)-3-isopropylamino-2-propanol or 1-(4-indolyloxy)-3-isopropylamino-2-propanol, or a non-toxic acid addition salt thereof which can be used pharmaceutically, as the beta-receptor-blocking component, together with L-tryptophane or a non-toxic salt thereof which can be used pharmaceutically, and which, because of their low degree of side effects, are particularly suitable for the treatment of sleep disorders.

A further subject of the present invention is the use, for the treatment of coronary heart diseases, of pharmaceutical preparations which contain a beta-receptor-blocking compound, such as one of the abovementioned compounds, especially one of the compounds with this type of action designated above as being preferred, above all 1-(2-allyloxy-phenoxy)-3-isopropylamino-2-propanol or a non-toxic acid addition salt thereof which can be used pharmaceutically, and L-tryptophane or a non-toxic salt thereof which can be used pharmaceutically, as the pharmaceutical active components.

The ratio of the beta-receptor-blocking compound to L-tryptophane, or to a non-toxic salt thereof which can be used pharmaceutically, in the new pharmaceutical preparations can vary within wide limits. In general, a ratio of about 1:2 to about 1:200 (by weight), especially a ratio of about 1:5 to about 1:100 (by weight), of the beta-receptor-blocking active compound to L-tryptophane, or to a non-toxic salt thereof which can be used pharmaceutically, is used.

The absolute dosage of the active components in the new pharmaceutical preparations also varies greatly and depends above all on the activity of the beta-receptor-blocking component to be used. In general, the new preparations contain from about 0.001 g to about 0.2 g, preferably, about 0.002 g to about 0.1 g, of the beta-receptor-blocking active compound and from about 0.2 g to about 2.0 g, preferably from about 0.4 g to about 1.5 g, of L-tryptophane or a non-toxic salt thereof which can be used pharmaceutically.

Thus, the preferred pharmaceutical preparations contain from about 0.01 g to about 0.1 g, preferably from about 0.02 g to about 0.08 g of 1-(2-allyloxy-phenoxy)-3-isopropylamino-2-propanol, optionally in the form of one of its optically active isomers, especially the L-antipodes, or of a non-toxic acid addition salt thereof which can be used pharmaceutically, or contain the same amounts, as indicated above, of 3-isopropylamino-1-(1-naphthyloxy)-2-propanol or of a non-toxic acid addition salt thereof which can be used pharmaceutically, or the same amounts, as indicated above, of 3-isopropylamino-1-[4-(2-methoxyethyl)-phenoxy]-2-propanol, or of a non-toxic acid addition salt thereof which can be used pharmaceutically, or the same amounts, as indicated above, of 1-(4-acetylamino-phenoxy)-3-isopropylamino-2-propanol, or of a non-toxic acid addition salt thereof which can be used pharmaceutically, or about 0.001 to 0.1 g, preferably from about 0.002 to about 0.010 g of 1-(4-indolyloxy)-3-isopropylamino-2-propanol, or of a non-toxic acid addition salt thereof which can be used pharmaceutically, and from about 0.2 g to about 2.0 g, preferably from about 0.4 g to about 1.5 g, of L-tryptophane or of a non-toxic salt thereof which can be used pharmaceutically.

In addition to the pharmacological active compounds, the new pharmaceutical preparations usually contain suitable excipients and auxiliaries which facilitate processing of the active compound into the preparations which can be used pharmaceutically. Preferably, the preparations, above all preparations which can be administered orally and which can be used for the preferred type of administration, such as tablets, dragees and capsules, and also preparations which can be administered rectally, such as suppositories, as well as suitable solutions for administration by injection or orally, contain from about 20% to 100%, preferably from about 50% to about 90%, of active compound together with the excipient.

The pharmaceutical preparations of the present invention are manufactured in a manner which is in itself known, for example by means of conventional mixing, granulating, dragée-making, dissolving or lyophilising processes. Thus, pharmaceutical preparations for oral use can be obtained by combining the active compounds with solid excipients, optionally granulating a resulting mixture and processing the mixture or granules, after adding suitable auxiliaries if desired or necessary, to give tablets or dragée cores.

Suitable excipients are, in particular, fillers, such as sugars, for example lactose or sucrose, mannitol or sorbitol, cellulose preparations and/or calcium phosphates, for example tricalcium phosphate or calcium hydrogen phosphate, as well as binders, such as starch pastes using, for example, maize starch, wheat starch, rice starch or potato starch, gelatine tragacanth, methylcellulose, hydroxypropylmethylcellulose, sodium carboxymethylcellulose and/or polyvinylpyrrolidone, and/or, if desired, disintegrating agents, such as the abovementioned starches, and also carboxymethyl-starch, cross-linked polyvinylpyrrolidone, agar or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragée cores are provided with suitable coatings, which, if desired, are resistant to gastric juices, and for this purpose, inter alia, concentrated sugar solutions, which optionally contain gum arabic, talc, polyvinylpyrrolidone, polyethylene glycol and/or titanium dioxide, lacquer solutions in suitable organic solvents or solvent mixtures or, in order to produce coatings resistant to gastric juices, solutions of suitable cellulose preparations, such as acetylcellulose phthalate or hydroxypropylmethylcellulose phthalate, are used. Dyestuffs or pigments can be added to the tablets or dragée coatings, for example for identification or in order to characterise different combinations of active compound doses.

Other pharmaceutical preparations which can be used orally are push-fit capsules made of gelatine, as well as soft, sealed capsules made of gelatine and a plasticiser, such as glycerol or sorbitol. The push-fit capsules can contain the active compounds in the form of granules, for example mixed with fillers, such as lactose, binders, such as starches, and/or lubricants, such as talc or magnesium stearate, and, optionally, stabilisers. In soft capsules, the active compounds are preferably dissolved or suspended in suitable liquids, such as fatty oils, liquid paraffin or liquid polyethylene glycols, it also being possible to add stabilisers.

Possible pharmaceutical preparations which can be used rectally are, for example, suppositories, which consist of a combination of the active compounds with a suppository base. Suitable suppository bases are, for example, natural or synthetic triglycerides, paraffin hydrocarbons, polyethylene glycols or higher alkanols. In addition it is also possible to use gelatine rectal capsules which consist of a combination of the active compounds with a base; possible base materials are, for example, liquid triglycerides, polyethylene glycols or paraffin hydrocarbons.

Suitable formulations for parenteral administration are, above all, aqueous solutions of the active compounds in a water-soluble form, for example in the form of water-soluble salts, and also suspensions of the active compounds, such as appropriate oily injection suspensions, for which suitable lipophilic solvents or vehicles, such as fatty oils, for example sesame oil, or synthetic fatty acid esters, for example ethyl oleate or triglycerides, are used, or aqueous injection suspensions, which contain substances which increase the viscosity, for exxample sodium carboxymethylcellulose, sorbitol and/or dextran, and optionally also contain stabilisers.

The examples which follow illustrate the invention described above; however, they are not intended to restrict the scope of the invention in any way.

EXAMPLE 1

Tablets containing 0.04 g of 1-(2-allyloxy-phenoxy)-3-isopropylamino-2-propanol hydrochloride and 1.0 g of L-tryptophane are manufactured as follows.

| Composition (for 1 tablet) | |
|---|---|
| 1-(2-allyloxy-phenoxy)-3-isopropylamino-2-propanol hydrochloride | 0.040 g |
| L-tryptophane | 1.000 g |
| maize starch | 0.095 g |
| hydroxypropylmethylcellulose (low viscosity) | 0.030 g |
| colloidal silica | 0.050 g |
| sodium carboxymethyl-starch | 0.080 g |
| magnesium stearate | 0.005 g |
| water | q.s. |

The tablets are manufactured as follows (for 1,000 tablets):

A mixture of 40 g of 1-(2-allyloxy-phenoxy)-3-isopropylamino-2-propanol hydrochloride, 1,000 g of L-tryptophane, 95 g of maize starch and 50 g of colloidal silica is worked into a moist mass with a solution of 30 g of hydroxypropylmethylcellulose in 300 g of demineralised water. This is forced through a sieve of 3 mm mesh width, dried at 45° C. for 30 minutes (fluidised-bed drier) and homogenized together with 80 g of sodium carboxymethyl-starch and 5 g of magnesium stearate through a sieve of 1 mm mesh width. The granules thus obtained are pressed to give capsule-shaped tablets 20.7 mm in length and 8.6 mm in width, which have a breaking groove.

EXAMPLE 2

Tablets containing 0.02 g of 1-(2-allyloxy-phenoxy)-3-isopropylamino-2-propanol hydrochloride and 0.5 g of L-tryptophane are manufactured as follows:

| Composition (for 1 tablet) | |
|---|---|
| 1-(2-allyloxy-phenoxy)-3-isopropylamino-2-propanol hydrochloride | 0.020 g |
| L-tryptophane | 0.500 g |
| maize starch | 0.050 g |
| hydroxypropylmethylcellulose (low viscosity) | 0.015 g |
| colloidal silica | 0.020 g |
| sodium carboxymethyl-starch | 0.040 g |
| magnesium stearate | 0.003 g |
| water | q.s. |

The tablets are manufactured according to the process indicated in Example 1; however, the resulting granules are pressed to give tablets 11.5 mm in diameter.

EXAMPLE 3

Tablets containing 0.02 g of L-1-(2-allyloxy-phenoxy)-3-isopropylamino-2-propanol hydrochloride and 1.0 g of L-tryptophane are manufactured as follows:

| Composition (for 1 tablet) | |
| --- | --- |
| L-1-(2-allyloxy-phenoxy)-3-isopropylamino-2-propanol hydrochloride | 0.020 g |
| L-tryptophane | 1.000 g |
| maize starch | 0.095 g |
| hydroxypropylmethylcellulose (low viscosity) | 0.030 g |
| colloidal silica | 0.050 g |
| sodium carboxymethyl-starch | 0.080 g |
| magnesium stearate | 0.005 g |
| water | q.s. |

The tablets are manufactured according to the process indicated in Example 1.

EXAMPLE 4

Tablets containing 0.04 g of 3-isopropylamino-1-(1-naphthyloxy)-2-propanol hydrochloride and 0.1 g of L-tryptophane are manufactured as follows:

| Composition (for 1 tablet) | |
| --- | --- |
| 3-isopropylamino-1-(1-naphthyloxy)-2-propanol hydrochloride | 0.040 g |
| L-tryptophane | 1.000 g |
| maize starch | 0.095 g |
| hydroxypropylmethylcellulose (low viscosity) | 0.030 g |
| colloidal silica | 0.050 g |
| sodium carboxymethyl-starch | 0.080 g |
| magnesium stearate | 0.005 g |
| water | q.s. |

The tablets are manufactured as described in Example 1 for 1,000 tablets.

EXAMPLE 5

Tablets containing 0.04 g of 3-isopropylamino-1-[4-(2-methoxyethyl)-phenoxy]-2-propanol tartrate and 1.0 g of L-tryptophane are manufactured as follows:

| Composition (for 1 tablet) | |
| --- | --- |
| 3-isopropylamino-1-[4-(2-methoxyethyl)-phenoxy]-2-propanol tartarate | 0.040 g |
| L-tryptophane | 1.000 g |
| maize starch | 0.095 g |
| hydroxypropylmethylcellulose (low viscosity) | 0.030 g |
| colloidal silica | 0.050 g |
| sodium carboxymethyl-starch | 0.080 g |
| magnesium stearate | 0.005 g |
| water | q.s. |

The tablets are manufactured as described in Example 1 for 1,000 tablets.

EXAMPLE 6

Tablets containing 0.04 g of 1-(4-acetylaminophenoxy)-3-isopropylamino-2-propanol hydrochloride and 1.0 g of L-tryptophane are manufactured as follows:

| Composition (for 1 tablet) | |
| --- | --- |
| 1-(4-acetylamino-phenoxy)-3-isopropylamino-2-propanol hydrochloride | 0.1 g |
| L-tryptophane | 1.000 g |
| maize starch | 0.095 g |
| hydroxypropylmethylcellulose (low viscosity) | 0.030 g |
| colloidal silica | 0.050 g |
| sodium carboxymethyl-starch | 0.080 g |
| magnesium stearate | 0.005 g |
| water | q.s. |

The tablets are manufactured as described in Example 1 for 1,000 tablets.

EXAMPLE 7

Tablets containing 0.005 g of 1-(4-indolyloxy)-3-isopropylamino-2-propanol and 1.0 g of L-tryptophane are manufactured as follows.

| Composition (for 1 tablet) | |
| --- | --- |
| 1-(4-indolyloxy)-3-isopropylamino-2-propanol | 0.005 g |
| L-tryptophane | 1.000 g |
| maize starch | 0.095 g |
| hydroxypropylmethylcellulose (low visosity) | 0.030 g |
| colloidal silica | 0.050 g |
| sodium carboxymethyl-starch | 0.080 g |
| magnesium stearate | 0.005 g |
| water | q.s. |

The tablets are manufactured as described in Example 1 for 1,000 tablets.

EXAMPLE 8

In place of the beta-receptor-blocking active components used in the above Examples 1 to 7, it is possible to use 3-isopropylamino-3-(3-methyl-phenoxy)-2-propanol, 1-(2-allyl-phenoxy)-3-isopropylamino-2-propanol, 3-isopropylamino-1-[4-(2-methylthioethoxy)-phenoxy]-2-propanol, 1-(9,10-ethano-9,10-dihydro-1-anthryloxy)-3-isopropylamino-2-propanol, 3-isopropylamino-1-[2-(1-pyrryl)-phenoxy]-2-propanol, 1-[2-(3,4-dimethoxyphenyl)-ethylamino]-3-(3-methyl-phenoxy)-2-propanol, 1-isopropylamino-3-(1,2,3,4-tetrahydro-1,4-ethano-5-naphthyloxy)-2-propanol, 1-tert.-butylamino-3-(1,2,3,4-tetrahydro-2,3-dihydroxy-5-napthyloxy)-2-propanol, 1-(7-indenyloxy)-3-isopropylamino-2-propanol, 1-(7-indanyloxy)-3-isopropylamino-2-propanol, 1-(5-methyl-8-cumaryloxy)-3-isopropylamino-2-propanol, 4-(3-isopropylamino-2-hydroxy-1-propyloxy)-2-methyl-indole or 2-tert.-butylamino-1-(7-ethyl-2-benzofuranyloxy)-ethanol, or a non-toxic acid addition salt thereof which can be used pharmaceutically.

I claim:

1. A pharmaceutical preparation suitable as hypnotic for inducing and prolonging sleep which contains a mixture of pharmacological active compounds comprising (1) a beta-receptor blocking compound selected from the group consisting of 3-isopropylamino-1-(1-naphthyloxy)-2-propanol, 3-isopropylamino-1-(3-methyl-phenoxy)-2-propanol, 1-(2-allylphenoxy)-3-isopropylamino-2-propanol, 1-(4-acetylamino-phenoxy)-3-isopropylamino-2-propanol, 1-(4-indolyloxy)-3-isopropylamino-2-propanol, 3-isopropylamino-1-[4-(2-methoxyethyl)-phenoxy]-2-propanol, 3-isopropylamino-1-[4-(2-methylthioethoxy)-phenoxy]-2-propanol, 1-(9,10-ethano-9,10-dihydro-1-anthryloxy)-3-isopropylamino-2-propanol, 3-isopropylamino-1-[2-(1-pyrryl)-phenoxy]-2-propanol, 1-[2-(3,4-dimethoxyphenyl)-ethylamino]-3-(3-methyl-phenoxy)-2-propanol, 1-isopropylamino-3-(1,2,3,4-tetrahydro-1,4-ethano-5- naphthyloxy)-propanol, 1-tert.-butylamino-3-(1,2,3,4-tetrahydro-2,3-dihydroxy-5-naphthyloxy)-2-propanol, 1-(7-indenyloxy)-3-isopropylamino-2-propanol, 1-(7-indanyloxy)-3-isopropylamino-2-propanol, 1-(5-methyl-8-cumaryloxy)-3-isopropylamino-2-propanol, 4-(3-isopropylamino-2-hydroxy-1-propyloxy)-2-methylindole, 2-tert.-butylamino-1-(7-ethyl-2-benzofuranyloxy)-ethanol and 1-(2-allyloxy-phenoxy)-3-isopropylamino-2-propanol in the form of racemates, optically active antipodes or a non-toxic acid addition salt thereof, which can be used pharmaceutically, and (2) L-tryptophane or a non-toxic salt thereof which can be used pharmaceutically, wherein the ratio of the beta-receptor blocking compound to L-tryptophane, or a non-toxic salt thereof which can be used pharmaceutically is of about 1:5 to about 1:100 by weight and which contains from about 20% to about 100% of active compounds together with an excipient.

2. A pharmaceutical preparation as claimed in claim 1 which comprises from about 0.001 g to about 0.2 g of the beta receptor-blocking compound and from about 0.2 g to about 2.0 g of the L-tryptophane compound.

3. A pharmaceutical preparation as claimed in claim 1, which comprises from about 0.005 g to about 0.1 g of the beta-receptor-blocking compound and from about 0.4 g to about 1.5 g of the L-tryptophane compound.

4. A pharmaceutical preparation as claimed in claim 1, which comprises from about 0.01 g to about 0.1 g of 1-(2-allyloxy-phenoxy)-3-isopropylamino-2-propanol or of a non-toxic acid addition salt thereof which can be used pharmaceutically, and from about 0.2 g to about 2.0 g of L-tryptophane, or of a non-toxic salt thereof which can be used pharmaceutically.

5. A pharmaceutical preparation as claimed in claim 1 which comprises from about 0.02 g to about 0.08 g of 1-(2-allyloxy-phenoxy)-3-isopropylamino-2-propanol, or of a non-toxic acid addition salt thereof which can be used pharmaceutically, and from about 0.4 g to about 1.5 g of L-tryptophane, or of a non-toxic salt thereof which can be used pharmaceutically.

6. A pharmaceutical preparation as claimed in claim 1, which comprises from about 0.01 g to about 0.1 g of 3-isopropylamino-1-(1-naphthyloxy)-2-propanol, or of a non-toxic acid addition salt thereof which can be used pharmaceutically, and from about 0.2 g to about 2.0 g of L-tryptophane, or of a non-toxic salt thereof which can be used pharmaceutically.

7. A pharmaceutical preparation as claimed in claim 1, which comprises from about 0.02 g to about 0.08 g of 3-isopropylamino-1-(1-naphthyloxy)-2-propanol, or of a non-toxic acid addition salt thereof which can be used pharmaceutically, and from about 0.4 g to about 1.5 g of L-tryptophane, or of a non-toxic salt thereof which can be used pharmaceutically.

8. A pharmaceutical preparation as claimed in claim 1, which comprises from about 0.01 g to about 0.1 g of 3-isopropylamino-1-[4-(2-methoxyethyl)-phenoxy]-2-propanol, or of a non-toxic acid addition salt thereof which can be used pharmaceutically, and from about 0.2 g to about 2.0 g of L-tryptophane, or of a non-toxic salt thereof which can be used pharmaceutically.

9. A pharmaceutical preparation as claimed in claim 1, which comprises from about 0.02 g to about 0.08 g of 3-isopropylamino-1-[4-(2-methoxyethyl)-phenoxy]-2-propanol, or of a non-toxic acid addition salt thereof which can be used pharmaceutically, and from about 0.4 g to about 1.5 g of L-tryptophane, or of a non-toxic salt thereof which can be used pharmaceutically.

10. A pharmaceutical preparation as claimed in claim 1, which comprises from about 0.01 g to about 0.1 g of 1-(4-acetylamino-phenoxy)-3-isopropylamino-2-propanol, or of a non-toxic acid addition salt thereof which can be used pharmaceutically, and from about 0.2 g to about 2.0 g of L-tryptophane, or of a non-toxic salt thereof which can be used pharmaceutically.

11. A pharmaceutical preparation as claimed in claim 1, which comprises from about 0.02 g to about 0.08 g of 1-(4-acetylamino-phenoxy)-3-isopropylamino-2-propanol, or of a non-toxic acid addition salt thereof which can be used pharmaceutically, and from about 0.4 g to about 1.5 g of L-tryptophane, or of a non-toxic salt thereof which can be used pharmaceutically.

12. A pharmaceutical preparation as claimed in claim 1, which comprises from about 0.001 g to about 0.020 g of 1-(4-indolyloxy)-3-isopropylamino-2-propanol, or of a non-toxic acid addition salt thereof which can be used pharmaceutically, and from about 0.2 g to about 2.0 g of L-tryptophane, or of a non-toxic salt thereof which can be used pharmaceutically.

13. A pharmaceutical preparation as claimed in claim 1, which comprises from about 0.002 g to about 0.010 g of 1-(4-indolyloxy)-3-isopropylamino-2-propanol, or of a non-toxic acid addition salt thereof which can be used pharmaceutically, and from about 0.4 g about 1.5 g of L-tryptophane, or of a non-toxic salt thereof which can be used pharmaceutically.

14. A pharmaceutical preparation as claimed in claim 1, which can be administered orally and which contains from about 50% to about 90% of active compounds together with an excipient.

15. A method for relieving sleep disorders in warm blooded animals in need of treatment which comprises the administration thereto, as a hypnotic for inducing and prolonging sleep the pharmaceutical preparation of claim 1.

* * * * *